United States Patent

Schleenstein et al.

[11] Patent Number: 5,883,291
[45] Date of Patent: Mar. 16, 1999

[54] HEAT EXCHANGE MEDIA FOR THE THERMAL CRACKING OF CARBAMIC ACID ESTERS

[75] Inventors: Dieter Schleenstein, Odenthal; Christian Rasp, Bergisch Gladbach; Georg Ronge, Düsseldorf; Oswald Wilmes, Köln, all of Germany

[73] Assignee: Bayer Aktiengesellschaft, Leverkusen, Germany

[21] Appl. No.: 812,610

[22] Filed: Mar. 6, 1997

[30] Foreign Application Priority Data

Mar. 15, 1996 [DE] Germany .................. 196 10 261.8
May 10, 1996 [DE] Germany .................. 196 18 828.8

[51] Int. Cl.⁶ .................................................. C07C 263/00
[52] U.S. Cl. ............................................................ 560/345
[58] Field of Search ............................................. 560/345

[56] References Cited

U.S. PATENT DOCUMENTS

| | | | |
|---|---|---|---|
| 3,734,941 | 5/1973 | Sydor | 260/453 P |
| 3,870,739 | 3/1975 | DeLaMater et al. | 260/453 P |
| 3,919,278 | 11/1975 | Rosenthal et al. | 260/453 P |
| 4,330,479 | 5/1982 | Merger et al. | 260/453 P |
| 4,386,033 | 5/1983 | König et al. | 260/453 P |
| 4,388,246 | 6/1983 | Sundermann et al. | 260/453 P |
| 4,482,499 | 11/1984 | Merger et al. | 260/453 P |
| 4,596,678 | 6/1986 | Merger et al. | 560/344 CM |
| 4,596,679 | 6/1986 | Hellbach et al. | 560/344 |
| 4,599,401 | 7/1986 | Koleske | 528/408 |
| 4,613,466 | 9/1986 | Merger et al. | 560/344 |
| 4,692,550 | 9/1987 | Engbert et al. | 560/345 |
| 4,748,226 | 5/1988 | Merger et al. | 528/85 |
| 5,043,471 | 8/1991 | Hammen et al. | 560/345 |
| 5,087,739 | 2/1992 | Bohmholdt et al. | 560/345 |
| 5,284,969 | 2/1994 | Hauner et al. | 560/345 |
| 5,360,931 | 11/1994 | Bohmholdt et al. | 560/344 |
| 5,386,053 | 1/1995 | Otterbach et al. | 560/344 |
| 5,554,787 | 9/1996 | Merger et al. | 560/355 |

FOREIGN PATENT DOCUMENTS

| | | |
|---|---|---|
| 323514 | 7/1989 | European Pat. Off. . |
| 524554 | 1/1993 | European Pat. Off. . |
| 4413580 | 10/1995 | Germany . |

*Primary Examiner*—Samuel Barts
*Attorney, Agent, or Firm*—Joseph C. Gil; Lyndanne M. Whalen

[57] ABSTRACT

Inert, thermally stable high-boiling solvents which have a defined boiling point or which boil over a narrow range are used as heat exchange media during thermal cracking of carbamic acid esters (urethane cracking).

4 Claims, No Drawings

HEAT EXCHANGE MEDIA FOR THE THERMAL CRACKING OF CARBAMIC ACID ESTERS

BACKGROUND OF THE INVENTION

This invention relates to a process for the thermal cracking of carbamic acid esters (urethane cracking) in which inert thermally stable high-boiling solvents having a defined boiling point or a narrow boiling range are used as heat exchange media.

A distinction can be made between the cracking of carbamic acid esters to form isocyanates in the gaseous and liquid phases and cracking in a fluidized bed. Cracking in the gas phase is described, for example, in EP-A-28,724; EP-A 100,047; EP-A 126,299; EP-A 126,300; EP-A 143,120; EP-A 261,604; EP-A 449,110; U.S. Pat. No. 3,734,941; and U.S. Pat. No. 3,870,739.

Cracking in the gas phase is a high-temperature process and is generally conducted at temperatures >300° C. in a vacuum of <25 mbar. The cost of the gas phase cracking process technology, the thermal loading of the starting materials and products, the requisite prior evaporation of the carbamic acid ester, and the catalytic effects of metal surfaces which are still not completely understood make gas phase cracking less advantageous than cracking in the liquid phase. In particular, there is a risk of blockage in the evaporator region due to the formation of deposits because the problem of transferring out higher molecular weight secondary products has not been solved.

Cracking in a fluidized bed is described in EP-A 78,005, for example. Processes such as these have high energy requirements and appear to be difficult to implement on an industrial scale. Use of such fluidized beds on an industrial scale cannot therefore be foreseen due to this interim state of development.

Compared to gas phase cracking, cracking in the liquid phase may be carried out at lower reaction temperatures (i.e., temperatures <300° C.). However, rapid separation of the reaction products is necessary to prevent the back-reaction of the isocyanate and the hydroxyl component to form carbamic acid esters and to reduce or prevent the formation of resin-like by-products which can form deposits in the apparatus used. The formation of higher molecular weight secondary products can be reduced by dilution with an inert solvent. The solvent also transfers these by-product components from the apparatus.

Many of the known processes can be distinguished by the type of reactor employed. A stirred reactor is used in the process disclosed in EP-A 355,443. A thin-film or tubular reactor is used in the processes described in EP-A-61,013, EP-A 92,738, and EP-A 396,977. A reactor with a fitted column is used in the processes taught in EP 323,514 and EP-A 524,554. A combined cracking and rectification column is used in the process disclosed in EP-A 568,782. Reaction columns are used in the process described in EP-A 542,106.

Another distinguishing feature of the known cracking processes is the presence or absence of a solvent during the cracking reaction.

Solvent-free cracking is described in EP-A 355,443, EP-A 568,782, EP-A 966,925 and EP-A 524,554. One disadvantage of such processes is that cracking proceeds in the column bottom, i.e. in the evaporator. In this heated region there is the risk of by-product formation due to the severe temperature gradients. In order to remove these by-products, high proportions (15 to 25% by weight) of the reactor charge have to be transferred out. Otherwise, caked deposits can occur which can result in a blockage of the reactor.

The problem of caked deposits is curbed by the addition of solvent (EP-A 61,103, EP-A 92,738, EP-A 323,514, and EP-A 542,106). The best yields are obtained when cracking is conducted in the stripping part of a combined cracking and rectification column. In this type of apparatus, the cracking reaction is prevented from proceeding in the evaporator region with the aid of a suitable high-boiling solvent. This solvent transfers the heat energy from the evaporator into the reaction zone by evaporation and condensation.

Cracking of a carbamic acid ester can be conducted in a cracking and rectification column so that no carbamic acid ester comes into contact with the heated surfaces of the evaporator. The apparatus can be operated in this manner for long periods. In contrast to the columns described in DE-A 4,231,417 and in EP-A 0,524,554, only a slight outward transfer of the column bottom content is necessary because no carbamic acid ester, cracking product or by-products can be detected analytically at the bottom of the column.

This process enables complete cracking (free from by-products) of the carbamic acid ester to be achieved in the distillation part of the column. Consequently, losses in yield are prevented and subsequent work-up is considerably simplified. Secondary reactions and caked deposits in the column bottom are prevented because reacting products do not reach the column bottom at all. Service lifetime of the apparatus is definitely prolonged.

The carbamic acid esters to be used in the process according to the invention are compounds corresponding to the general formula $R^1(NHCOOR^2)_n$, in which $R^1$ is an aliphatic hydrocarbon radical containing a total of from about 4 to 12 carbon atoms and, optionally, bearing inert substituents; a cycloaliphatic hydrocarbon radical containing a total of from about 6 to 15 carbon atoms and, optionally, bearing inert substituents; an araliphatic hydrocarbon radical containing a total of from about 7 to 10 carbon atoms and, optionally, bearing inert substituents, or an aromatic hydrocarbon radical containing a total of from about 6 to 15 carbon atoms and, optionally, inert substituents;

$R^2$ is an aliphatic hydrocarbon radical containing from about 1 to 20 carbon atoms, a cycloaliphatic hydrocarbon radical containing from about 5 to 15 carbon atoms or an aromatic hydrocarbon radical containing from about 6 to 15 carbon atoms and n is an integer of from 2 to 5.

The carbamic acid esters preferably used in the process according to the invention are those corresponding to the above formula in which $R^1$ is an aliphatic hydrocarbon radical containing a total of from 4 to 12 and, more preferably, from 5 to 10 carbon atoms; a cycloaliphatic hydrocarbon radical containing from 6 to 15 carbon atoms; a xylylene radical or an aromatic hydrocarbon radical containing a total of from 6 to 15 carbon atoms and, optionally, bearing methyl substituents and/or methylene bridges;

$R^2$ is an aliphatic hydrocarbon radical containing from 1 to 6 and, more particularly, from 1 to 4 carbon atoms; a cyclohexyl radical; or a phenyl radical; and n is an integer of from 2 to 4.

Particularly preferred carbamic acid esters for the process according to the invention are those corresponding to the general formula $$R^1(NHCOOR^2)_2$$

in which $R^1$ is the hydrocarbon radical linking the isocyanate groups of 1,6-diisocyanatohexane, 1-isocyanato-3,3,5-trimethyl-5-isocyanatomethyl cyclo-hexane, 2,4-diisocyanatotoluene, 2,6-diisocyanatotoluene, 2,2'-, 2,4'- or 4-4'-diisocyanatodiphenyl methane, 2,4'- or 4,4'-diisocyanatodicyclohexyl methane or 1,5-diisocyanatonaphthalene and $R^2$ is a $C_{1-4}$ alkyl radical.

Examples of suitable carbamic acid esters are
1-(butoxycarbonylamino)-3,3,5-trimethyl-5-(butoxycarbonylaminomethyl)-cyclohexane,
1-(methoxycarbonylamino)-3,3,5-trimethyl-5-(methoxycabonylaminomethyl)-cyclohexane,
1-methyl-2,4-bis-(methoxycarbonylamino)-benzene,
1-methyl-2,6-bis-(methoxycarbonylamino)-benzene,
1-methyl-2,4-bis-(butoxycarbonylamino)-benzene,
1-methyl-2,6-bis-(butoxycarbonylamino)-benzene,
1,10-bis-(methoxycarbonylamino)-decane,
1,12-bis-(butoxycarbonylamino)-dodecane,
1,12-bis-(methoxycarbonylamino)-dodecane,
1,12-bis-(phenoxycarbonylamino)-dodecane,
1,3-bis-(ethoxycarbonylaminomethyl)-benzene,
1,3-bis-(methoxycarbonylamino)-benzene,
1,3-bis-[(methoxycarbonylamino)-methyl)]-benzene,
1,3,6-tris-(methoxycarbonylamino)-hexane,
1,3,6-tris-(phenoxycarbonylamino)-hexane,
1,4-bis-(ethoxycarbonylamino)-butane,
1,4-bis-(ethoxycarbonylamino)-cyclohexane,
1,5-bis-(butoxycarbonylamino)-naphthalene,
1,6-bis-(methoxycarbonylamino)-hexane,
1,6-bis-(ethoxycarbonylamino)-hexane,
1,6-bis-(butoxycarbonylamino)-hexane,
1,5-bis-(methoxycarbonylamino)-pentane,
1,6-bis-(methoxymethylcarbonylamino)-hexane,
1,8-bis-(ethoxycarbonylamino)-octane,
1,8-bis-(phenoxycarbonylamino)-4-(phenoxycarbonylaminomethyl)-octane,
2,2'-bis-(4-propoxycarbonylaminophenyl)-propane,
2,4'-bis-(ethoxycarbonylamino)-diphenyl methane,
2,4-bis-(methoxycarbonylamino)-cyclohexane,
4,4'-bis-(ethoxycarbonylamino)-dicyclohexane methane,
2,4'-bis-(ethoxycarbonylamino)-diphenyl methane,
4,4'-bis-(methoxycarbonylamino)-2,2'-dicyclohexyl propane,
4,4'-bis-(methoxycarbonylamino)-biphenyl,
4,4'-bis-(butoxycarbonylamino)-2,2'-dicyclohexyl propane,
4,4'-bis-(phenoxycarbonylamino)-dicyclohexyl methane and
4,4'-bis-(phenoxycarbonylamino)-diphenyl methane.

The "butoxy groups" mentioned are iso- and n-butoxy groups.

Solvents which are suitable for conducting cracking in columns of this type may be liquid or solid. Examples of such solvents are given in EP-A 542,106. The boiling points of suitable solvents under the conditions of pressure in the bottom of the column are at least 10° C., preferably at least 40° C., above the boiling points of the isocyanates and alcohols which form the basis of the carbamic acid esters that are to be cracked. These solvents satisfy the following requirements:

a) under the conditions of cracking, they substantially dissolve both the carbamic acid esters used as starting materials and the secondary products of the isocyanates which are formed as by-products of the reaction;

b) they are substantially thermally stable under the conditions of cracking;

c) they are substantially chemically inert to the carbamic acid esters used and to the isocyanates formed;

d) they are substantially distillable under the conditions of cracking;

e) they can be substantially separated by distillation from the reaction by-products; and f) they can be recycled.

U.S. Pat. No. 3,919,278; EP-A 323,514; EP-A 61,013; and EP 92,738 disclose specific examples of high-boiling substances which satisfy these requirements. These disclosed solvents can be used in the practice of the present invention after they have been purified. Examples of other suitable solvents include the various isomeric benzyl toluenes, terphenyls, phenoxybiphenyls, phthalic acid di(ar)alkyl esters and o-phosphoric acid tri(ar)alkyl esters with 1 to 10 carbon atoms in the (ar)alkyl esters in each case, and mixtures of compounds of this type.

Technical dibenzyl toluene, benzyl-n-butyl phthalate, technical terphenyl and partially hydrogenated terphenyls, phenoxybiphenyls and isomeric mixtures thereof are particularly suitable for use in cracking and rectification columns. However, commercially available high-boiling solvents or heat transfer media do not exhibit a defined boiling point but exhibit a boiling range. This results in the separation by distillation of the solvent mixture in the cracking column and in a broad temperature profile. In the extreme case, low-boiling constituents are distilled off with the isocyanate or alcohol cracking products and the higher-boiling products become concentrated in the bottom of the column.

SUMMARY OF THE INVENTION

It is an object of the present invention to provide suitable solvents or solvent mixtures for thermal cracking of carbamic acid esters in a combined cracking and rectification column.

It is also an object of the present invention to provide a thermal cracking process for carbamic acid esters in which a high boiling solvent acts as a heat exchange medium.

These and other objects which will be apparent to those skilled in the art are accomplished by thermally cracking a carbamic acid ester in the presence of a high boiling solvent which has a defined boiling point or a very narrow boiling range.

DETAILED DESCRIPTION OF THE PRESENT INVENTION

It has been found that with the aid of a suitable, high-boiling solvent, the thermal cracking reaction of a carbamic acid ester is prevented from proceeding in the evaporator region of a combined cracking and rectification column. The solvent transfers heat energy from the evaporator into the reaction zone by evaporation and condensation and thus functions as a heat exchange medium. In contrast to commercially available heat transfer media which are resistant to high temperatures, the high-boiling solvents used in the practice of the present invention should have a boiling range (temperature window) which is as narrow as possible. A narrow boiling range makes it possible to select a temperature which is low enough that by-product formation does not occur or occurs only to a slight extent but also high enough that cracking proceeds sufficiently rapidly. The desired "temperature window" in the column in the area where reaction occurs is obtained by adjusting the absolute pressure in that part of the reaction column. A solvent with a narrow boiling range is preferably used when this available "temperature window" for the selected carbamic acid esters is narrow. When the "temperature window" is wider, cracking can also be achieved using the heat transfer media with wide boiling ranges which have been used in known processes.

It has now surprisingly been found that, compared with cracking or heat exchange media which exhibit a boiling range, an optimally matched "cracking medium" which has a sharp boiling point reduces the temperature drop in a cracking column and thus enables the bottom temperature to be reduced. This helps prevent formation of high-boiling substances in the cracking column bottom and makes the cracking process technically controllable.

The present invention relates to the use of a solvent which has a defined boiling point (pure substance) or which has a boiling range of <10° C., preferably <6° C., most preferably <3° C., at the operating pressure. The solvent is generally obtained as a distillation cut from thermally stable liquids for the thermal cracking of carbamic acid esters.

Distillation cuts of commercially available heat transfer oils are preferred. Examples of such transfer oils include: terphenyl, dibenzyl toluene, dibenzyl benzene and phenoxybiphenyl. The ortho-, meta- and para- isomers of phenoxybiphenyl are particularly preferred.

By using distillation cuts with a narrow boiling range, the temperature difference in the reaction part of a cracking column such as that which is described below can be reduced at a given loading (i.e. at a given pressure drop) from 16° C. (Marlotherm S) to 7.5° C. (ortho-phenoxybiphenyl). Consequently, the bottom temperature of the column can be reduced by 4° C. (for the same cracking output and with an unchanged average temperature in the reaction part) and the risk of the formation of by-products and cracking products in the column bottom is considerably reduced. Cracking products can be found in the column bottom if carbamic acid esters reach the column bottom (e.g., due to technical problems) and react further there.

It is essential that the reaction proceed as a reactive rectification with the inert solvent. The solvent vapor rises from the evaporator and makes the energy for the endothermic reaction and for partial evaporation available in the stripping part by condensation.

The cracking products rise in the form of vapors and are thus directly removed from the liquid reaction phase. During the cracking of multi-functional carbamic acid esters, the partially cracked intermediate product may be deposited in the region between the feed and the side take-off and can be recycled into the reaction zone for complete cracking. The separation of the hydroxyl component and the isocyanate occurs in the enrichment part above the side take-off of the reactor. Liquid retention should be as short as possible due to the tendency for back-reaction to occur.

In order to prevent back-reactions, the enrichment part and the middle part of the rectification column can be operated at a pressure which is up to 900 mbar less than the reaction part of the column. The specific pressure differential will depend on the column bottom pressure. Separation of the pressure levels may optionally be achieved by using separate apparatus for the enrichment and middle parts of the column.

Back reaction can also be prevented by using a pressure which is reduced in the enrichment part of the reactor only to reduce the temperature and slow back reaction.

Rectification columns which are made up of a stripping part having a sufficiently long dwell time and an enrichment part with a shorter dwell time are suitable apparatus for the practice of the present invention. The dwell time in the stripping part must be matched to the kinetics of cracking and mass transfer and is therefore strongly dependent on the specific system (i.e., the specific substances present). The dwell time generally ranges from about 1 to about 1000 minutes, preferably from about 5 to about 200 minutes. Dwell time is defined as the ratio of the liquid retention in the stripping part to the volume flow of the liquid phase feed. Packings with a low pressure drop and with a high retention in combination with a solvent having a narrow boiling range are preferred because a temperature which is approximately constant over the reaction part of the column and which is freely selectable by way of the absolute pressure employed is achieved. The temperature in the reaction zone should preferably be selected to be within a temperature range in which the cracking reaction proceeds sufficiently rapidly and in which the formation of by-products that cannot be recycled does not occur at all or occurs only to a slight extent.

The columns useful in the practice of the present invention have a reflux at the top, at least one side take-off for the partial or complete removal of the liquid phase, and a bottom outlet.

Any of the commonly available evaporators are suitable as evaporators for operating a column in accordance with the present invention. For lasting operation, the heating surfaces must be well wetted and flushed all round. Bubble cap bases, sieve plates, and ordered or random packings are possible baffles in the middle part and/or in the stripping part and/or in the enrichment part of the column. Ordered packings are preferred.

As in the processes disclosed in EP-A 54,817; EP-A 92,738; and EP-A 355,443, the cracking products of the present invention may be separated by reflux condensers, but they are preferably separated by rectification.

The reactor feed is composed of the carbamic acid ester, optionally a catalyst and/or the inert solvent which is used in accordance with the present invention, and optionally the by-products formed in a cyclic process in which a carbamic acid ester is produced from an amine, a carbonyl source (e.g., oxides of carbon) or carboxylic acid derivatives (preferably urea and/or carbamic acid esters or dialkyl carbonates), and a hydroxyl component. Some or all of the recycled solvent may optionally be introduced directly into the bottom of the column.

The feed stream to the cracking column is generally composed of the main stream from the upstream process step and optionally, a) the partial stream which is low in by-products and which results from the bottom discharge of the cracking column after the outward transfer of higher-boiling by-products, and optionally, b) the bottom discharge of the purification column, and optionally, c) fresh solvent, and optionally, d) the top product from the purification column. The feed stream is preheated to a temperature up to 250° C. above the melting temperature of the carbamic acid ester but which is preferably 50° C. below the reaction temperature. The feed is introduced into the column above the stripping part.

In order to increase the reaction rate, cracking of the carbamic acid esters can be conducted in the presence of catalysts. Catalysts are not normally necessary in the process. If catalysts are used, they are generally used in amounts of up to 10% by weight, preferably up to 3% by weight, based on the weight of the carbamic acid ester. Examples of suitable catalysts include metals, metal oxides, inorganic or organic metal compounds, and acidic additives. Examples of suitable catalysts are given in U.S. Pat. No. 3,919,279; U.S. Pat. No. 4,388,246; DE-A 3,277,748; DE-A 3,248,018; DE-A 3,314,790; U.S. Pat. No. 4,873,365; EP-A 323,514; EP-A 126,299; EP-A 566,925; and EP-A 568,782.

The cracking process of the present invention may also be catalyzed heterogeneously by using packing material or packing body surfaces which have a suitable catalytic action.

The cracking column is operated at a bottom pressure of from about 2 to about 1000 mbar; preferably from about 20 to about 200 mbar. The bottom temperature is from about 150° to about 400° C., preferably from about 220° to about 300° C. The optimal bottom temperature is dependent upon the boiling temperature of the solvent, and should be selected so that secondary reactions of the carbamic acid ester only occur to a slight extent. The reflux ratio at the top of the column is between 0.2 and 20, preferably between 2 and 10. The reflux ratio at the side stream take-off is between 0 and 40, preferably between 5 and 20.

The bottom discharge transfers by-products and any high-boiling impurities which may have been fed into the reactor (e.g. together with the carbamic acid ester) out of the reactor. The amount of solvent to be fed into or discharged from the reactor need only be sufficient to maintain a predetermined by-product concentration in the column bottom. In contrast to the processes disclosed in EP-A 0,524,554 and DE-A 4,231,417, complete cracking of the carbamic acid ester normally occurs in the first pass through the column in the process of the present invention. Consequently, no starting material normally needs to be recycled. High-boiling impurities can be transferred out of the bottom take-off stream in a downstream apparatus in any manner known to those in the art. Examples of suitable known methods for removing high boiling impurities include vacuum distillation, preferably by thin-film distillation and/or by falling film distillation.

The solvent-rich stream is fed back into the cracking column. The isocyanate-rich side stream from the cracking column is subsequently subjected to a purification distillation step.

The bottoms from the purification distillation step are generally admixed with the feed to the cracking column. If the proportion of higher molecular weight reaction by-products is higher, the bottoms may also be completely or partially recycled to the urethane production stage or they may be transferred out.

The invention is further illustrated but is not intended to be limited by the following example in which all parts and percentages are by weight, unless otherwise specified.

EXAMPLE 0.91 kg/hour of a mixture of hexamethylene-di-n-butylurethane-1,6 (HDU-B) was continuously fed into a cracking column together with 0.3 kg/hour of ortho-phenoxybiphenyl (content >99% by GC, boiling range <3° C. at the operating pressure). The HDU-B and ortho-phenoxybiphenyl were fed into the column at a point above the stripping part.

The column was made up of an evaporator with 4 horizontally disposed heater plug inserts. Above the evaporator, over a length of 8.1 m in the stripping part, there was an ordered packing having a diameter of 70 mm and a liquid retention capacity of around 1500 ml in total. The feed inlet was situated above the reaction zone. The HDU-B was metered in at 120° C. and the solvent was metered in at 160° C. The middle part of the column had a diameter of 70 mm and was filled with cloth packing pieces over an effective height of 990 mm. Above this cloth packing was the side stream take-off, followed by an effective length of 850 mm of cloth packing with a diameter of 50 mm. The top of the column was composed of a liquid separator and a water-cooled condenser. The column was insulated.

The top reflux ratio was 7, and the side stream reflux ratio was 10. The top pressure was 85 mbar and the bottom temperature was 260° C.

0.3 kg/hour of liquid were taken off from the column bottom. As analyzed by supercritical fluid chromatography (SFC), this liquid from the column bottom only contained the heat transfer medium. HDU-B and its secondary products were not detected (detection limit 0.1%). The same result was obtained by IR analysis.

The liquid which drained off into the bottom from the distillation column, and which was sampled, was just as pure (i.e., no impurities were found either by SFC or by IR analysis).

The side stream of 0.4 kg/hour was composed of 98.2% by weight of hexa-methylene diisocyanate (HDI), 1.6% by weight of a semi-cracked product represented by Formula (I)

$$BuOCONH-(CH_2)_6-NCO \qquad (I),$$

0.1% by weight of ortho-phenoxybiphenyl and 0.1% by weight of BuOH.

The top take-off stream amounted to 0.43 kg/hour and had a composition of 99.5% BuOH, 0.2% by weight HDU-B and 0.3% by weight of (I).

The yield (maximum possible amount of HDI less the losses in the column bottom and top) in this test was considerably greater than 99%. In this respect, the content of (I) in the side stream was not assessed as a loss, since (I) can be recovered via the reflux from the purification column. The yield can be further increased if the top product is recycled.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for cracking a carbamic acid ester in which the carbamic acid ester is subjected to cracking conditions in the presence of a solvent which is a distillation cut from a thermally stable liquid having a defined boiling point or a boiling range of less than 10° C. at the cracking pressure.

2. The process of claim 1 in which the solvent is a high-boiling distillation cut of a heat transfer oil selected from the group consisting of partially hydrogenated terphenyl, dibenzyl toluene and phenoxybiphenyl.

3. The process of claim 1 in which the solvent is high-boiling distillation cut of a heat transfer oil selected from the group consisting of partially hydrogenated terphenyl, dibenzyl benzene, phenoxybiphenyl and o-phenoxybiphenyl which has a boiling range of less than 3° C. at the operating pressure.

4. The process of claim 1 in which the cracking is conducted in a reactive rectification column.

* * * * *